United States Patent [19]
Julius et al.

[11] Patent Number: 6,130,347
[45] Date of Patent: Oct. 10, 2000

[54] PREPARATION OF CYANOACETIC ESTERS

[75] Inventors: Manfred Julius, Limburgerhof; Rolf Schneider, Mannheim; Klaus Mundinger, Limburgerhof; Jakob Fischer, Kirchdorf, all of Germany

[73] Assignee: BASF Aktiengesellschaft, Ludwigshafen, Germany

[21] Appl. No.: 09/432,204

[22] Filed: Nov. 2, 1999

[30] Foreign Application Priority Data

Nov. 3, 1998 [DE] Germany ............................ 198 50 624

[51] Int. Cl.⁷ ................................................. C07C 255/17
[52] U.S. Cl. ............................................................. 558/342
[58] Field of Search ............................................... 558/342

[56] References Cited

U.S. PATENT DOCUMENTS 2,985,682  5/1961  Raffelson .
4,322,369  3/1982  Desbois et al. .

FOREIGN PATENT DOCUMENTS 32 078       7/1981   European Pat. Off. .
1 210 789    2/1966   Germany .
1 272 914    7/1968   Germany .
1 951 032    5/1970   Germany .
96/38409    12/1996   WIPO .

OTHER PUBLICATIONS

J. Adhesion Sci. Tech., vol. 4, No. 9, 733–750, (1990) Vijayalakshmi et al.

*Primary Examiner*—Joseph M McKane
*Assistant Examiner*—Joseph Murray
*Attorney, Agent, or Firm*—Keil & Weinkauf

[57] ABSTRACT

Cyanoacetic esters are prepared by reacting a corresponding monochloroacetic ester with hydrogen cyanide in the presence of a base, where the base is a compound selected from the group consisting of tertiary amines, salts of carbonic acid, salts of carbonic acid monoesters, salts of carboxylic acids, amidines, guanidines and aromatic N-heterocyclic compounds.

7 Claims, No Drawings

PREPARATION OF CYANOACETIC ESTERS

The present invention relates to a process for the preparation of cyanoacetic esters by reacting a corresponding monochloroacetic ester with hydrogen cyanide in the presence of a base.

Cyanoacetic esters are important intermediates for the preparation of performance chemicals, active ingredients (for example caffeine) and light stabilizers (see, for example, WO-A-96 38409) and are generally prepared in two variants starting from monochloroacetic acid:

a) 1. Conversion of monochloroacetic acid into the corresponding sodium salt (for example by reaction with sodium hydroxide solution). 2. Cyanidation of the sodium salt of monochloroacetic acid to the sodium salt of cyanoacetic acid (for example by reaction with NaCN). 3. Liberation of cyanoacetic acid, and 4. Esterification of cyanoacetic acid.

b) 1. Esterification of monochloroacetic acid, and 2. Cyanidation of the monochloroacetic ester in accordance with the following scheme:

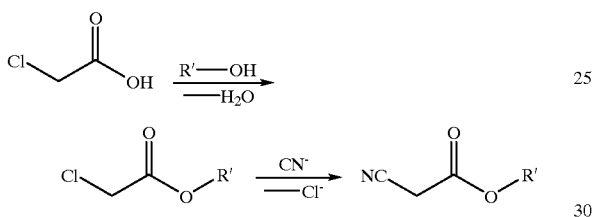

Variant b) is shorter and, owing to the lower number of process steps, more economical than variant a). In addition, the amount of salts formed, which have to be disposed of in a complex process, is lower.

The esterification of monochloroacetic acid by reaction with an alcohol is known from the literature or is carried out analogously to the processes known to the person skilled in the art (see, for example, J. Adhesion Sci. Technol., Vol. 4, No. 9, page 734 (1990) and Example No. 15).

DE-A-12 10 789 and DE-A-12 72 914 disclose the reaction of monochloroacetic esters with hydrogen cyanide and alkali metal cyanide or alkali metal alkoxide in a molar ratio of 2:1:1 at about 60° C. with reaction times of about 1 h. At a monochloroacetic ester conversion of about 50%, selectivities for the formation of the corresponding cyanoacetic ester of about 85% are described.

According to DE-A-19 51 032, cyanoacetic ester yields of up to 80% are achieved for the reaction of monochloroacetic esters with excess NaCN in aqueous acetonitrile at reaction temperatures of from 50 to 80° C. and reaction durations of from 4 to 7 hours.

EP-A-32 078 describes the reaction of monochloroacetic esters with ECN and NaCN in a molar ratio of about 1:1.2:1.6 in anhydrous acetonitrile in the presence of tert-alkoxyalkylamines as catalyst. The cyanoacetic ester yields in this process are from 93 to 95% at reaction temperatures of from 0 to 20° C. and reaction durations of from 5 to 10 hours.

These processes have the disadvantages of the need to handle solid sodium cyanide and the complex recovery of solid cyanide compounds employed in excess. Furthermore, the sodium cyanide required must first be prepared in a complex manner from hydrogen cyanide and sodium hydroxide solution.

U.S. Pat. No. 2,985,682 describes a process for the preparation of cyanoacetic esters by reacting monohaloacetic esters with HCN and ammonia. According to Example 1 of this patent specification, a yield of 50% and a selectivity (based on the n-butyl monochloroacetate employed) of 89% are achieved in the preparation of n-butyl cyanoacetate at a reaction time of at least 7 hours. The disadvantage of this process is the low space-time yield.

It is an object of the present invention to find an alternative, economical process for the preparation of cyanoacetic esters starting from corresponding monochloroacetic esters by reaction thereof with hydrogen cyanide.

We have found that this object is achieved by a process for the preparation of cyanoacetic esters by reacting a corresponding monochloroacetic ester with hydrogen cyanide in the presence of a base, wherein the base is a compound selected from the group consisting of tertiary amines, salts of carbonic acid, salts of carbonic monoesters, salts of carboxylic acids, amidines, guanidines and aromatic N-heterocyclic compounds.

Examples of tertiary amines which can be employed in accordance with the invention as base are the following:

trimethylamine, triethylamine, ethyldimethylamine, tri-n-propylamine, tri-isopropylamine, diethyl-isopropylamine, ethyl-diisopropylamine, tri-n-butylamine, tri-n-hexylamine, tri-n-octylamine, tri-(2-ethylhexyl)amine, N,N,N',N'-tetramethylethylenediamine, cyclopentyldimethylamine, cyclopentyldiethylamine, cyclohexyldimethylamine, cyclohexyldiethylamine, ethyldicyclohexylamine, N-methylpyrrolidine, N-ethylpyrrolidine, N-methylpiperidine, N-ethylpiperidine, N-methylhexamethyleneimine, N,N'-dimethylpiperazine, N,N'-diethylpiperazine, 1,4-diazabicyclo[2.2.2]octane, N-methylmorpholine, N-ethylmorpholine, N,N-dimethylaniline, N,N-diethylaniline and 4-dimethylaminopyridine. Preference is given to tertiary alkylamines, in particular trialkylamines.

Examples of salts of carbonic acid which can be employed in accordance with the invention as base are the following:

metal carbonates, preferably alkali metal carbonates, such as lithium carbonate, sodium carbonate and potassium carbonate, metal hydrogen carbonates, preferably alkali metal hydrogen carbonates, such as lithium hydrogen carbonate, sodium hydrogen carbonate and potassium hydrogen carbonate, quaternary ammonium carbonates, for example tetraalkylammonium carbonates, such as bis(tetramethylammonium) carbonate, bis(tetraethylammonium) carbonate, bis(tetra-n-butylammonium) carbonate, bis(methyltriethylammonium) carbonate, bis(benzyltrimethylammonium) carbonate, bis(2-hydroxyethyltrimethylammonium) carbonate or basic anionic exchangers of type I (containing —CH$_2$—N(CH$_3$)$_3{}^+$ groups) or of type II (containing —CH$_2$—N$^+$(CH$_3$)$_2$—CH$_2$CH$_2$OH groups), charged with carbonate ions, quaternary ammonium hydrogencarbonates, for example tetraalkylammonium hydrogen carbonates, described in EP-A-671 384, such as tetramethylammonium hydrogencarbonate, tetraethylammonium hydrogencarbonate, tetra-n-butylammonium hydrogencarbonate, benzyltrimethylammonium hydrogencarbonate, methyltributylammonium hydrogencarbonate, methyltridodecyl-ammonium hydrogencarbonate, methyltriethylammonium hydrogencarbonate, ethyltributylammonium hydrogencarbonate, phenyltrimethylammonium hydrogencarbonate, phenyldimethylethylammonium hydrogencarbonate, tris(2-hydroxyethyl)methylammonium hydrogencarbonate, 2-hydroxyethyltrimethylammonium hydrogencarbonate, choline hydrogencarbonate or basic anionic exchangers of type I (containing —$CH_2$—$N(CH_3)_3^+$ groups) or of type II (containing —$CH_2$—$N^+(CH_3)_2$—$CH_2CH_2OH$ groups), charged with hydrogen carbonate ions, quaternary phosphonium carbonates, for example tetraalkylphosphonium carbonates, such as bis(tetramethylphosphonium) carbonate, bis(tetraethylphosphonium) carbonate and bis(benzyltrimethylphosphonium) carbonate, and quaternary phosphonium hydrogencarbonates, for example tetraalkylphosphonium hydrogencarbonates, such as tetramethylphosphonium hydrogencarbonate, tetraethylphosphonium hydrogencarbonate, tetra-n-butylphosphonium hydrogencarbonate, benzyltrimethylphosphonium hydrogencarbonate, methyltributylphosphonium hydrogencarbonate, methyltridodecylphosphonium hydrogencarbonate, methyltriethylphosphonium hydrogencarbonate, ethyltributylphosphonium hydrogencarbonate, phenyltrimethylphosphonium hydrogencarbonate, phenyldimethylethylphosphonium hydrogencarbonate, tris(2-hydroxyethyl)methylphosphonium hydrogencarbonate and 2-hydroxyethyltrimethylphosphonium hydrogencarbonate.

Examples of salts of carbonic acid monoesters which can be employed in accordance with the invention as base are the following:

metal alkyl carbonates, preferably alkali metal alkyl carbonates, such as lithium methyl carbonate, sodium methyl carbonate, potassium methyl carbonate, lithium ethyl carbonate, sodium ethyl carbonate and potassium ethyl carbonate, quaternary ammonium alkyl carbonates, for example tetraalkylammonium alkyl carbonates as described in EP-A-671 384, such as tetramethylammonium methyl carbonate, methyltri-n-butylammonium methyl carbonate, tetraethylammonium methyl carbonate, benzyltrimethylammonium methyl carbonate, methyltridodecylammonium methyl carbonate, tetra-n-butylammonium methyl carbonate, tetra-n-butylammonium methyl carbonate, methyltriethylammonium methyl carbonate, phenyltrimethylammonium methyl carbonate, phenyldimethylethylammonium methyl carbonate, tris(2-hydroxyethyl)methylammonium methyl carbonate, 2-hydroxyethyltrimethylammonium methyl carbonate or basic anionic exchangers of type I (containing —$CH_2$—$N(CH_3)_3^+$ groups) or of type II (containing —$CH_2$—$N^+(CH_3)_2$—$CH_2CH_2OH$ groups) charged with alkyl carbonate ions, for example methyl carbonate ions, and quaternary phosphonium alkyl carbonates, for example, tetraalkylphosphonium alkyl carbonates, such as tri-n-butylmethylphosphonium methyl carbonate, triethylmethylphosphonium methyl carbonate and triphenylmethylphosphonium methyl carbonate.

Examples of salts of carboxylic acids which can be employed in accordance with the invention as base are the following:

metal carboxylates, preferably metal carboxylates of aliphatic carboxylic acids, such as formic acid, acetic acid, propionic acid, 2-ethylhexanoic acid, and adipic acid. Particular preference is given to alkali metal carboxylates, such as lithium acetate, sodium acetate, potassium acetate and sodium propionate.

Preference is furthermore given to quaternary ammonium carboxylates, preferably quaternary ammonium carboxylates of aliphatic carboxylic acids, such as those mentioned above, for example tetraalkylammonium carboxylates, such as tetramethylammonium acetate, tetramethylammonium propionate, tetraethylammonium acetate and benzyltrimethylammonium acetate. The term 'salts of carboxylic acids' here likewise covers the so-called 'internal salts' (betaines) of carboxylic acids, such as quaternary ammonium compounds of amino acids, such as trimethyl ammoniumacetate and 1,3-dimethylimidazolium-4-carboxylate.

Examples of amidines which can be employed in accordance with the invention as base are the following:

peralkylated amidines, such as acetic acid methylamide methylimide, benzoic acid methylamide methylimide, acetic acid methylamide phenylimide and bicyclic amidines, such as 1,5-diazabicyclo[4.3.0]non-5-ene (DBN), 1,8-diazabicyclo[5.4.0]undec-7-ene (DBU), 1,6-diazabicyclo[5.5.0]dodec-6-ene, 1,7-diazabicyclo[6.5.0]tridec-7-ene, 1,8-diazabicyclo[7.4.0]tridec-8-ene, 1,8-diazabicyclo[7.5.0]tetradec-8-ene, 1,5-diazabicyclo[4.4.0]dec-5-ene (DBD), 1,8-diazabicyclo[5.3.0]dec-7-ene, 1,10-diazabicyclo[7.3.0]dodec-9-ene, 1,10-diazabicyclo[7.4.0]tridec-9-ene, 2-methyl-1,5-diazabicyclo[4.3.0]non-5-ene, 3-methyl-1,5-diazabicyclo[4.3.0]non-5-ene, 7-methyl-1,5-diazabicyclo[4.3.0]non-5-ene, 7-benzyl-1,5-diazabicyclo[4.3.0]non-5-ene, 11-methyl-1,8-diazabicyclo[5.4.0]undec-7-ene, 10-methyl-1,8-diazabicyclo[5.4.0]undec-7-ene, 6-methyl-1,8-diazabicyclo[5.4.0]undec-7-ene, 6-benzyl-1,8-diazabicyclo[5.4.0]undec-7-ene, 2-methyl-1,5-diazabicyclo[4.4.0]dec-5-ene, 3-methyl-1,5-diazabicyclo[4.4.0]dec-5-ene, 7-methyl-1,5-diazabicyclo[4.4.0]dec-5-ene and 7-benzyl-1,5-diazabicyclo[4.4.0]dec-5-ene. Preference is given to DBN, DBD and DBU, particularly preferably to DBU and DBN.

Examples of guanidines which can be employed in accordance with the invention as base are the following:

peralkylated guanidines, such as pentamethylguanidine, N-ethyl-N,N',N',N"-tetramethylguanidine, N"-ethyl-N,N,N',N'-tetramethylguanidine, N,N-diethyl-N',N',N"-trimethylguanidine, N,N"-diethyl-N,N',N'-trimethylguanidine, pentaethylguanidine, 2-phenyl-1,1,3,3-tetramethylguanidine, 2-isopropyl-1,1,3,3-tetramethylguanidine, 2-tert-butyl-1,1,3,3-tetramethylguanidine, pentaphenylguanidine, 2-methyl-1,1,3,3-tetrabutylguanidine, 2-phenyl-1,1,3,3-tetrabutylguanidine, 1,1,3,3-tetramethyl-2-octylguanidine, 2-decyl-1,1,3,3-tetramethylguanidine, pentaisopropylguanidine and 2-tert-butyl-1,1,3,3-tetraisopropylguanidine.

Examples of aromatic N-heterocyclic compounds which can be employed in accordance with the invention as base are the following:

pyridine, 2-methylpyridine, 3-methylpyridine, 4-methylpyridine, 4-tert-butylpyridine, 2,6-dimethylpyridine, 4,4'-bipyridyl, 2,2'-bipyridyl, quinoline, isoquinoline, pyrazine, pyrimidine, s-triazine, N-methylimidazole and N-methylpyrrole.

Quaternary ammonium hydrogencarbonates and carbonates can be prepared, for example, in situ in accordance with EP-A-502 707 by reaction of corresponding tetraalkylammonium halides with alkali metal hydrogencarbonates, or alkali metal carbonates.

The preparation of basic ion exchangers charged with hydrogen carbonate ions is described, for example, in WO 95/20559.

Quaternary phosphonium hydrogencarbonates and carbonates can be prepared, for example, in situ in accordance with EP-A-502 707 by the reaction of corresponding tetraalkylphosphonium halides with alkali metal hydrogen carbonates or alkali metal carbonates.

Quaternary ammonium and phosphonium alkyl carbonates can be prepared in accordance with EP-A-291 074 and the methods cited therein, for example by reaction of a tertiary amine or phosphine with a dialkyl carbonate in approximately stoichiometric amounts. The resultant solution can be employed directly, without a further process step, as base in the process according to the invention.

The synthesis of peralkylated amidines is described, for example, in Houben Weyl, Methoden der organischen Chemie, Volume E5, pp. 1304–8 (1985); S. Patai, The chemistry of amidines and imidates, pp. 283f (1975); H. Oediger et al., Synthesis, pp. 591–8 (1972); H. Oediger et al., Chem. Ber. 99, pp. 2012–16 (1966); L. Xing-Quan, J. Nat. Gas Chem. 4, pp. 119–27 (1995) and the earlier German Patent Application No. 19752935.6.

The synthesis of peralkylated guanidines is described, for example, in U.S. Pat. No. 2,845,459; Justus Liebigs Ann. Chem. 445, p. 70 (1925); ibd. 438, p. 163 (1924); ibd. 455, pp. 163f (1927); ibd. 455, p. 152 (1927); Chem. Ber. 97, 1232–45 (1964); tetrahedron 26, 1805–20 (1979); Chem. Ber. 37, 965 (1904); tetrahedron 46 (6), 1839–48 (1990); Liebigs Ann. Chem., 108–26 (1984); ibd. 2178–93 (1985); FR-A-25 09 724; U.S. Pat. No. 4,358,613; GB 1,290,470 and U.S. Pat. No. 3,399,233.

The preparation of the betaine 1,3-dimethyl-imidazolium-4-carboxylate by reaction of 1-methylimidazole with dimethyl carbonate is described below in Example No. 16 (cf. earlier German Patent Application No. 19836477.6).

Cyanoacetic esters of the formula I

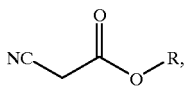

(I)

where R is an unsaturated or saturated, aliphatic, cycloaliphatic or heterocyclic radical, aromatic or heteroaromatic radical or arylalkyl radical, where the radical R can carry substituents which are inert under the reaction conditions, are of particular economic interest.

The process according to the invention is therefore preferably used for the preparation of the cyanoacetic esters I by reacting a monochloroacetic ester of the formula II

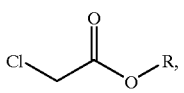

(II)

with hydrogen cyanide.

The radical R can be varied broadly, where the following may be mentioned by way of example:

linear or branched, saturated, aliphatic radicals, preferably $C_{1-20}$-alkyl, particularly preferably $C_{1-12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl and isododecyl, very particularly preferably $C_{1-8}$-alkyl, such as methyl, ethyl, n-propyl, isopropyl, n-butyl, isobutyl, sec-butyl, tert-butyl and 2-ethylhexyl, linear or branched mono- or polyunsaturated aliphatic radicals, preferably $C_{2-20}$-alkenyl and $C_{3-20}$-alkinyl, particularly preferably $C_{2-12}$-alkenyl and $C_{3-12}$-alkinyl, such as ethenyl, 2-propen-1-yl, 2-propen-2-yl, 2-buten-1-yl, 2-buten-2-yl, 3-buten-1-yl, 3-buten-2-yl, 2-penten-1-yl, 4-penten-1-yl, 2-hexen-1-yl, 5-hexen-1-yl, 2-propyn-1-yl, 2-butyn-1-yl, 3-butyn-1-yl, 1-butyn-3-yl, 1-butyn-3-methyl-3-yl, 2-pentyn-1-yl, 4-pentyn-1-yl, 2-hexyn-1-yl, 5-hexyn-1-yl, 1-pentyn-3-methyl-3-yl and 1-octyn-4-ethyl-3-yl, saturated cycloaliphatic radicals, preferably $C_{3-8}$-cycloalkyl, such as cyclopropyl, cyclobutyl, cyclopentyl, cyclohexyl, cycloheptyl and cyclooctyl, particularly preferably cyclopentyl, cyclohexyl and cyclooctyl, very particularly preferably cyclopentyl and cyclohexyl, unsaturated cycloaliphatic radicals, preferably $C_{5-12}$-cycloalkenyl, particularly preferably $C_{5-8}$-cycloalkenyl, such as 1-cyclopentenyl, 3-cyclopentenyl, 1-cyclohexenyl, 3-cyclohexenyl, 1-cycloheptenyl and 1-cyclooctenyl, heterocyclic radicals, preferably $C_{3-15}$-heterocycloalkyl, such as N-alkylpiperidine-3-yl, N-alkylpiperidin-4-yl, N,N'-dialkylpiperazin-2-yl, tetrahydrofuran-3-yl, N-alkylpyrrolidin-3-yl, aromatic radicals, preferably $C_{6-20}$-aryl, such as phenyl, 1-naphthyl, 2-naphthyl, 1-anthryl, 2-anthryl, 9-anthryl, particularly preferably phenyl, 1-naphthyl and 2-naphthyl, especially preferably phenyl, heteroaromatic radicals, preferably $C_{3-15}$-heteroaryl, such as 2-pyridinyl, 3-pyridinyl, 4-pyridinyl, quinolinyl, pyrazinyl, pyrrol-3-yl, thienyl, imidazol-2-yl, 2-furanyl and 3-furanyl, arylalkyl radicals, preferably $C_{7-20}$-arylalkyl, such as benzyl, 1-phenethyl, 2-phenethyl, 1-naphthylmethyl, 2-naphthylmethyl, phenanthrylmethyls, 4-tert-butylphenylmethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, where, in these cases, the radical R can carry substituents which are inert under the reaction conditions, such as $C_{1-20}$-alkyl, $C_{1-20}$-alkoxy, $C_{6-20}$-aryloxy and halogen. The number of these substituents in R can, depending on the nature of the radical, be from 0 to 5, preferably 0 to 3, in particular 0, 1 or 2. Possible substituents are the following:

$C_{1-20}$-alkyl, as defined above, $C_{1-20}$-alkoxy, preferably $C_{1-8}$-alkoxy, such as methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy, such as methoxy, ethoxy, n-propoxy, isopropoxy, n-butoxy, isobutoxy, sec-butoxy and tert-butoxy, $C_{6-20}$-aryloxy, such as phenoxy, 1-naphthoxy and 2-naphthoxy, preferably phenoxy, halogen, such as fluorine, chlorine and bromine.

The process according to the invention for the preparation of cyanoacetic esters can be carried out as follows:

For example,
a) a mixture of the corresponding monochloroacetic ester can be initially introduced with hydrogen cyanide, if desired in the presence of an inert solvent, and the base, if desired in an inert solvent, can subsequently be metered in, or
b) a mixture of the base with hydrogen cyanide, if desired in the presence of an inert solvent, can be initially introduced, and the corresponding monochloroacetic ester, if desired in an inert solvent, can subsequently be metered in, or
c) a mixture of the base with the corresponding monochloroacetic ester, if desired in the presence of an inert solvent, can be initially introduced, and hydrogen cyanide, if desired in an inert solvent, can subsequently be metered in, or
d) the base in the presence of an inert solvent can be initially introduced, and a mixture of the corresponding monochloroacetic ester with hydrogen cyanide, if desired in an inert solvent, can subsequently be metered in.

Variants a), b) and d) are preferred.

The process can be carried out at reaction temperatures of from −78 to 200° C., preferably from −30 to 100° C., particularly preferably from −25 to 80° C., very particularly preferably from 0 to 60° C.

The reaction pressure (measured in absolute terms) is generally 30 from 0.05 to 2 MPa (0.5 to 20 bar), preferably from 0.09 to 1 MPa (0.9 to 10 bar), particularly preferably atmospheric pressure.

The base is generally employed in amounts of from 50 to 300 mol %, preferably from 75 to 150 mol %, particularly preferably from 95 to 105 mol %, very particularly preferably 100 mol %, based on the monochloroacetic ester employed.

In the process according to the invention, the hydrogen cyanide is generally employed in amounts of from 50 to 800 mol %, based on the monochloroacetic ester. Larger excesses of hydrogen cyanide are also possible.

The molar ratio between the two starting materials hydrogen cyanide and monochloroacetic ester is generally from 0.75 to 6:1, preferably from 0.9 to 5:1, particularly preferably from 1 to 4:1, very particularly preferably from 2 to 4:1.

Any unreacted hydrogen cyanide or hydrogen cyanide employed in excess can be recovered from a crude reaction product by distillation and recycled.

The bases used according to the invention allow particularly short residence times of the reaction mixture in the reactor (=reaction time) at the same time as good to very good yields, selectivities and high space-time yields. Depending on the selected reaction conditions, the residence times are generally from 10 minutes to a few hours, preferably from 0.5 to 5 hours, particularly preferably from 0.5 to 3 hours.

Furthermore, the process according to the invention virtually completely avoids the 'dimerization' and 'trimerization' of the monochloroacetic ester to the undesired esters III and IV

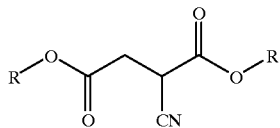

(III)

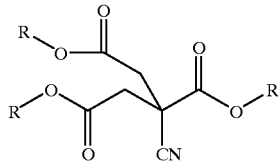

(IV)

which is known as a side reaction under basic conditions, particularly if the hydrogen cyanide is employed in a molar excess, based on the monochloroacetic ester.

The process according to the invention can also be carried out continuously. For example, a continuous process procedure can be carried out by feeding the base, if desired together with an inert solvent, continuously into a reactor in which a mixture of the corresponding monochloroacetic ester is reacted continuously with hydrogen cyanide, if desired in the presence of a solvent.

Suitable reaction vessels or reactors for the process according to the invention are, for example, stirred-tank reactors, tubular reactors, stirred-tank cascades and mixing circuits.

The process according to the invention is preferably carried out in the absence of water.

In some cases, it may prove advantageous to carry out the reaction according to the invention in the presence of from 0.5 to 10 mol %, preferably from 1 to 5 mol %, based on the monochloroacetic ester, of a catalyst selected from the group consisting of bis(dialkylaminoalkyl)ethers, for example, bis-(2-dimethylaminoethyl)ether, and tris(alkoxyalkyl)amines, for example tris(methoxyethyl)amine (=$(MeOCE_2CH_2)_3N$), tris(ethoxyethyl)amine, tris(methoxyethoxyethyl)amine (=TDA-1)

TDA-1

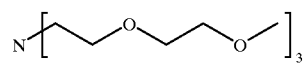

and tris(ethoxyethoxyethyl)amine (=TDA-2).

The process according to the invention can be carried out in the presence or absence of inert solvents.

Suitable inert solvents are ethers, such as diethyl ether, methyl tert-butyl ether, tetrahydrofuran and dioxane, nitriles, such as acetonitrile and propionitrile, aliphatic hydrocarbons, such as n-pentane, pentane isomer mixtures, n-hexane, hexane isomer mixtures, n-heptane, heptane isomer mixtures, n-octane, octane isomer mixtures, cycloaliphatic hydrocarbons, such as cyclopentane, cyclohexane, cycloheptane and cyclooctane, alcohols, preferably $C_1$- to $C_4$-alkanols, such as methanol, ethanol, n-propanol, isopropanol, n-butanol, isobutanol and tert-butanol, amides, such as dimethylformamide, dimethylacetamide, N-methylpyrrolidone, ureas, such as N,N'-dimethylethylene urea, N,N'-dimethylpropylene urea, N,N,N',N'-tetra-n-butyl urea, carbonates, such as ethylene carbonate and propylene carbonate, sulfolane, dimethyl sulfoxide or carbon dioxide in liquid or supercritical state.

The process according to the invention is preferably carried out in the presence of polar aprotic solvents, such as dimethyl formamide, dimethylacetamide, acetonitrile and dimethyl sulfoxide.

If tertiary amines, amidines, guanidines or aromatic N-heterocyclic compounds are used as base, the hydrochloride of the base precipitated from the crude reaction mixture or precipitated by addition of a nonpolar aprotic solvent, such as pentane or cyclohexane, can, if desired, be separated off after the reaction is complete, for example by filtration.

The cyanoacetic ester is generally isolated in pure form by fractional rectification of the crude reaction product or by crystallization/recrystallization of the cyanoacetic ester.

Recovered unreacted starting materials and solvents can be fed back into the synthesis.

The base can be re-liberated from the base hydrochloride separated off, if desired, from the reaction product, for example triethylamine hydrochloride, cyclohexyldimethylamine hydrochloride or diisopropylethylamine hydrochloride, by methods known to the person skilled in the art and then re-employed in the process according to the invention.

EXAMPLES

The GC conditions used in Example Nos. 1 to 15 were as follows: column: 30 m DB-1; film thickness 1 μm; temperature program: 50 to 300° C., 10° C./min, 35 min, 300° C.

The purity of the 2-ethylhexyl monochloroacetate employed in Example Nos. 1 to 9 was, according to GC, greater than 99%. Regarding the synthesis of this ester, see Example No. 15.

The purity of the ethyl monochloroacetate employed in Example Nos. 10 to 14 was, according to GC, greater than 99%.

In Example Nos. 1 to 14, the conversion and reaction selectivity data are always based on the 2-ethylhexyl monochloroacetate or ethyl monochloroacetate employed and were determined by gas chromatography in the resultant crude reaction product. To this end, the samples taken of the crude product were frozen in dry ice (−78° C.) until the gas-chromographic analysis.

Example 1

20.65 g (100 mmol) of 2-ethylhexyl monochloroacetate, 2.7 g (100 mmol) of freshly distilled hydrogen cyanide and 0.97 g (3 mmol) of tris(dioxa-3,6-heptyl)amine (=TDA-1) were introduced into 70 ml of dry acetonitrile at 0° C. under an argon atmosphere. A solution of 12.7 g (100 mmol) of dimethylcyclohexylamine in 30 ml of dry acetonitrile was subsequently metered in with stirring over the course of about 1 hour, the reaction mixture being kept at a temperature of from 0 to 5° C. Analysis of the resultant crude product showed a conversion of 86.4% and a selectivity for 2-ethylhexyl cyanoacetate of 50.3%.

Example 2

Performance of the reaction analogously to Example 1, with the difference that the reaction was carried out at −20° C., gave a conversion of 85.5% and a selectivity for 2-ethylhexyl cyanoacetate of 52.3%.

Example 3

20.65 g (100 mmol) of 2-ethylhexyl monochloroacetate and 2.7 g (100 mmol) of freshly distilled hydrogen cyanide were introduced into 70 ml of dry acetonitrile at 20° C. under an argon atmosphere. A solution of 15.5 g (100 mmol) of 1,8-diazabicyclo[5.4.0]-undec-7-ene (DBU) in 30 ml of dry acetonitrile was subsequently metered in with stirring over the course of about 1 hour, the reaction mixture being kept at a temperature of 20° C. by cooling. Analysis of the resultant crude product showed a conversion of 93.6% and a selectivity for 2-ethylhexyl cyanoacetate of 47.0%.

Example 4

10.3 g (50 mmol) of 2-ethylhexyl monochloroacetate and 1.3 g (50 mmol) of freshly distilled hydrogen cyanide were introduced into 40 ml of dry acetonitrile at 20° C. under an argon atmosphere. A solution of 5.05 g (50 mmol) of triethylamine in 30 ml of dry acetonitrile was subsequently metered in with stirring over the course of about 1 hour, the reaction mixture being held at a temperature of 20° C. Analysis of the resultant crude product showed a conversion of 54.1% and a selectivity for 2-ethylhexyl cyanoacetate of 68.0%. After a post-reaction time of 4 hours at 20° C., the conversion was 61.9% and the selectivity for 2-ethylhexyl cyanoacetate was 72.2%.

Example 5

Performance of the reaction analogously to Example 4, with the difference that the reaction was carried out at 50° C., gave a conversion of 57.3% and a selectivity for 2-ethylhexyl cyanoacetate of 66.7%. After a post-reaction time of 4 h at 50° C., the conversion was 70.5% and the selectivity for 2-ethylhexyl cyanoacetate was 68.8%.

Example 6

Performance of the reaction analogously to Example 4, with the difference that the reaction was carried out using 6.46 g (50 mmol) of N-ethyldiisopropylamine (Hunig base), gave a conversion of 33.2% and a selectivity for 2-ethylhexyl cyanoacetate of 73.5%. After a post-reaction time of 5 hours at 20° C., the conversion was 42.1% and the selectivity for 2-ethylhexyl cyanoacetate was 74.8%.

Example 7

10.3 g (50 mmol) of 2-ethylhexyl monochloroacetate and 5.61 g (27 mmol) of bis(tetramethylamonium)carbonate were introduced into 40 ml of dry acetonitrile at 20° C. under an argon atmosphere. After the mixture had been stirred for 15 minutes, a solution of 1.3 g (50 mmol) of freshly distilled hydrogen cyanide in 40 ml of dry acetonitrile was metered in with continued stirring over the course of about 1 hour, the reaction mixture being kept at a temperature of 20 to 25° C. by cooling from time to time. Analysis of the resultant crude product showed a conversion of 50.3% and a selectivity for 2-ethylhexyl cyanoacetate of 72.4%. After a post-reaction time of 5.5 hours at 20° C., the conversion was 69.3% and the selectivity for 2-ethylhexyl cyanoacetate was 78.4%.

Example 8

1.3 g (50 mmol) of freshly distilled hydrogen cyanide and 7.45 g (50 mmol) of tetramethylammonium methylcarbonate were introduced into 40 ml of dry acetonitrile at 20° C. under an argon atmosphere. A solution of 10.3 g (50 mmol) of 2-ethylhexyl monochloroacetate in 30 ml of dry acetonitrile was subsequently metered in with stirring over the course of about 1 hour, the reaction mixture being held at a temperature of 20° C. and then stirred for a further 1 hour at 20° C. Analysis of the resultant crude product showed a conversion of 91.0% and a selectivity for 2-ethylhexyl cyanoacetate of 74.3%.

Example 9

1.3 g (50 mmol) of freshly distilled hydrogen cyanide and 6.4 g (46 mmol) of 1,3-dimethylimidazolium-4-carboxylate were introduced into 40 ml of dry acetonitrile at 20° C. under an argon atmosphere. A solution of 10.3 g (50 mmol) of 2-ethylhexyl monochloroacetate in 30 ml of dry acetonitrile was subsequently metered in with stirring over the course of about 1 hour, the reaction mixture being held at a temperature of from 24 to 30° C. Analysis of the resultant crude product showed a conversion of 90.4% and a selectivity for 2-ethylhexyl cyanoacetate of 86.7%. After a post-reaction time of 1 hour at 20° C., the conversion was 93.1% and the selectivity for 2-ethylhexyl cyanoacetate was 88.0%.

Example 10

10.6 g (0.1 mol) of anhydrous sodium carbonate were suspended in 50 ml of dry dimethylacetamide at 50° C. with stirring, and a mixture of 12.25 g (0.1 mol) of ethyl monochloroacetate and 2.7 g (0.1 mol) of distilled anhydrous hydrogen cyanide was metered in over the course of 30 minutes. The reaction proceeded exothermically, and consequently the reaction mixture briefly warmed to 55° C. Stirring was continued at 50° C. Analysis of the resultant crude product showed, after an overall reaction time of 3 hours, a conversion of 75.4% and a selectivity for ethyl cyanoacetate of 83.5%. After an overall reaction time of 4 hours, the conversion was 88.1% and the selectivity for ethyl cyanoacetate was 77.0%.

Example 11

On performance of the experiment as described in Example 10, with the difference that a mixture of 12.25 g (0.1 mol) of ethyl monochloroacetate and 5.4 g (0.2 mol) of distilled anhydrous hydrogen cyanide was metered in over the course of 60 minutes, analysis of the resultant crude product after an overall reaction time of 1 h showed a conversion of 63.2% and a selectivity for ethyl cyanoacetate of 92.0%. After an overall reaction time of 2 hours, the conversion was 92.1% and the selectivity for ethyl cyanoacetate was 91.1%.

Example 12

On performance of the experiment as described in Example 10, with the difference that a mixture of 12.25 g (0.1 mol) of ethyl monochloroacetate and 8.1 g (0.3 mol) of distilled anhydrous hydrogen cyanide was metered in over the course of 45 minutes. Analysis of the resultant crude product after an overall reaction time of 45 minutes showed a conversion of 65.0% and a selectivity for ethyl cyanoacetate of 95.2%. After an overall reaction time of 2 hours, the conversion was 96.1% and the selectivity for ethyl cyanoacetate was 94.1%.

Example 13

On performance of the experiment as described in Example 10, with the difference that a mixture of 12.25 g (0.1 mol) of ethyl monochloroacetate and 10.8 g (0.4 mol) of distilled anhydrous hydrogen cyanide was metered in over the course of 60 minutes. Analysis of the resultant crude product after an overall reaction time of 1 h showed a conversion of 77.8% and a selectivity for ethyl cyanoacetate of 96.4%. After an overall reaction time of 2 hours, the conversion was 97.5% and the selectivity for ethyl cyanoacetate was 96.2%.

Example 14

On performance of the experiment as described in Example 10, with the difference that the reaction was carried out at 40° C. and a mixture of 12.25 g (0.1 mol) of ethyl monochloroacetate and 8.1 g (0.3 mol) of distilled anhydrous hydrogen cyanide was metered in over the course of 60 minutes. Analysis of the resultant crude product after an overall reaction time of 3 hours showed a conversion of 81.9% and a selectivity for ethyl cyanoacetate of 95.2%.

After an overall reaction time of 5 hours, the conversion was 92.5% and the selectivity for ethyl cyanoacetate was 94.0%.

Example 15

Synthesis of 2-ethylhexyl monochloroacetate A mixture of 630 g of a 75% strength aqueous solution of monochloroacetic acid (5.0 mol), 250 ml of toluene and 5 g of conc. sulfuric acid was heated to the boil with stirring on a water separator, and 693 g (5.33 mol) of 2-ethyl-1-hexanol were added over the course of 105 minutes. The refluxing was then continued for a further 6 hours, during which a total of 246 g of water (99.4% of theory) were separated off. The reaction solution was then cooled and washed with saturated aqueous $NaHCO_3$ solution and the organic phase was separated off and subjected to fractional rectification in a packed column (length 50 cm) at mbar. At a pass-over temperature of 117° C. 880.6 g of 2-ethylhexyl monochloroacetate were obtained as a colorless liquid having a purity of 99.43% (according to GC). Yield: 85%.

Example 16

Preparation of 1,3-dimethylimidazolium 4-carboxylate (norzooanemonin)

0.9 mol (73.8 g) of 1-methylimidazole and 0.9 mol (81.0 g) of dimethylcarbonate were introduced at room temperature into an autoclave. The batch was subsequently warmed to 140° C. and stirred at this temperature for 20 hours (inherent pressure: about 0.5 MPa). Cooling to room temperature left a thick yellow suspension. The crystals were filtered off and dried in an oil-pump vacuum. Crude weight: 119.4 g (=94.7% crude yield). The crystals were recrystallised from an approximately 1/1 ethanol/methanol mixture, giving white crystals, which were filtered off and dried in a high vacuum. Weight: 48.9 g. The mother liquor was evaporated to dryness. The yellow oily residue remaining was re-taken up in hot 1/1 ethanol/methanol mixture and precipitated at low temperature, giving a further 53.9 g of product. Overall yield: 102.8 g (81.5%).

Characterisation of the product:

Melting point: 240° C. (decomposition). MS (electron spray ionisation ESI, direct inlet): M=141 (M+H)$^+$. Elemental analysis: Calculated: C 51.4; E 5.8; N 20.0; 0 22.8 $C_6H_8N_2O_2$; MG=140.14 Found: C 51.3; H 5.7; N 19.9; O 23.4. $^1$H-NMR (400 MHz, $D_2O$) δ (ppm)=3.98 (3 E); 4.12 (3H); 7.88 (1H); 1 H exchanges in $D_2O$. $^{13}$C-NMR (100.61 MHz, $D_2O$) δ (ppm)=38.55 (methyl); 38.65 (methyl); 129.03 (CH); 133.59 (C—COO$^-$); 140.82 (t, C-D coupling); 165.8 (COO$^-$).

IR (KBr), [cm$^{-1}$]: 3451 ss, 1621 ss.

We claim:

1. A process for the preparation of cyanoacetic esters by reacting a corresponding monochloroacetic ester with hydrogen cyanide in the presence of a base, wherein the base is a compound selected from the group consisting of tertiary amines, salts of carbonic acid, salts of carbonic acid monoesters, salts of carboxylic acids, amidines, guanidines and aromatic N-heterocyclic compounds.

2. A process as claimed in claim 1, wherein the base is a compound selected from the group consisting of alkali metal carbonates, quaternary ammonium carbonates, quaternary ammonium alkyl carbonates and tertiary alkylamines.

3. A process as claimed in claim 1, wherein the base is sodium carbonate or 1,3-dimethylimidazolium-4-carboxylate.

4. A process as claimed in claim 1, wherein the molar ratio between hydrogen cyanide and monochloroacetic ester is from 1 to 4:1.

5. A process as claimed in claim 1, wherein the reaction is carried out at temperatures of from −25 to 80° C.

6. A process as claimed in claim 1, wherein the reaction is carried out in the presence of from 75 to 150 mol % of the base, based on the monochloroacetic ester employed.

7. A process as claimed in claim 1, wherein the reaction is carried out in the presence of a catalyst selected from the group consisting of bis(dialkylaminoalkyl) ethers and tris(alkoxyalkyl)amines.

* * * * *